(12) United States Patent
Van Der Heide et al.

(10) Patent No.: US 8,779,180 B2
(45) Date of Patent: Jul. 15, 2014

(54) PROCESS FOR REMOVING AN ALKANOL IMPURITY FROM AN ORGANIC CARBONATE STREAM

(75) Inventors: Evert Van Der Heide, Amsterdam (NL); Garo Garbis Vaporciyan, Houston, TX (US); Cornelis Leonardus Maria Vrouwenvelder, Amsterdam (NL)

(73) Assignee: Shell Oil Company, Houston, TX (US)

(*) Notice: Subject to any disclaimer, the term of this patent is extended or adjusted under 35 U.S.C. 154(b) by 175 days.

(21) Appl. No.: 13/124,752

(22) PCT Filed: Oct. 16, 2009

(86) PCT No.: PCT/EP2009/063606
§ 371 (c)(1),
(2), (4) Date: May 18, 2011

(87) PCT Pub. No.: WO2010/046320
PCT Pub. Date: Apr. 29, 2010

(65) Prior Publication Data
US 2011/0213173 A1    Sep. 1, 2011

(30) Foreign Application Priority Data

Oct. 20, 2008    (EP) ................................. 08167025

(51) Int. Cl.
*C07C 68/06* (2006.01)
*C07C 68/08* (2006.01)
*C07C 69/96* (2006.01)

(52) U.S. Cl.
CPC ............... *C07C 68/065* (2013.01); *C07C 68/08* (2013.01); *C07C 69/96* (2013.01)
USPC ....................................................... 558/276

(58) Field of Classification Search
None
See application file for complete search history.

(56) References Cited

U.S. PATENT DOCUMENTS

| | | | |
|---|---|---|---|
| 3,642,858 A | 2/1972 | Frevel et al. | 260/463 |
| 3,803,201 A | 4/1974 | Gilpin et al. | 260/463 |
| 4,062,884 A | 12/1977 | Romano et al. | 260/463 |
| 4,508,927 A | 4/1985 | Bhise et al. | 568/858 |
| 4,691,041 A | 9/1987 | Duranleau et al. | 558/277 |
| 5,359,118 A | 10/1994 | Wagner et al. | 558/277 |
| 5,508,442 A | 4/1996 | Wagner et al. | 549/228 |
| 6,197,918 B1* | 3/2001 | Uno et al. | 528/196 |

FOREIGN PATENT DOCUMENTS

| | | | | |
|---|---|---|---|---|
| BE | 1006039 | * | 4/1994 | |
| EP | 0001082 | | 6/1978 | C07C 69/96 |
| EP | 0274953 | | 7/1988 | B01J 23/02 |
| EP | 0180387 | | 10/2005 | C07D 301/02 |
| EP | 1760059 | | 3/2007 | C07C 27/02 |
| JP | 2002371037 | | 12/2002 | B01D 3/14 |
| JP | 2003300917 | | 10/2003 | B01D 3/38 |

OTHER PUBLICATIONS

English translation of BE 1006039, (1994). Obtained Aug. 11, 2013 from <http://worldwide.espacenet.com/>.*
Machine translation of JP 2003-300917, obtained from <http://worldwide.espacenet.com/>, Accessed Feb. 23, 2014.*
Knifton, John F. et al.: "Ethylene Gylcol-Dimethyl Carbonate Cogeneration"; Journal of Molecular Catalysis, 67; pp. 389-399; 1991.

* cited by examiner

*Primary Examiner* — Alicia L Otton

(57) ABSTRACT

The invention relates to a process for removing an alkanol impurity from a stream containing an organic carbonate and the alkanol impurity, comprising contacting the stream with a catalyst to effect reaction of the alkanol impurity with the organic carbonate.

10 Claims, No Drawings

PROCESS FOR REMOVING AN ALKANOL IMPURITY FROM AN ORGANIC CARBONATE STREAM

PRIORITY CLAIM

The present application claims priority from PCT/EP2009/063606, filed 16 Oct. 2009, which claims priority from European Application EP 08167025.9, filed 20 Oct. 2008.

FIELD OF INVENTION

The present invention relates to a process for removing an alkanol impurity from a stream containing an organic carbonate and the alkanol impurity.

BACKGROUND

Examples of organic carbonates are cyclic alkylene carbonates (such as ethylene carbonate) and non-cyclic dialkyl carbonates (such as diethyl carbonate). It is well known to make cyclic alkylene carbonate by reaction of alkylene oxide (such as ethylene oxide) with carbon dioxide in the presence of a suitable catalyst. Such processes have been described for example in U.S. Pat. No. 4,508,927 and U.S. Pat. No. 5,508,442.

Dialkyl carbonates can be produced by reaction of alkylene carbonate with alkanol. Where alkylene carbonate (such as ethylene carbonate) is reacted with alkanol (such as ethanol), the products are dialkyl carbonate (such as diethyl carbonate) and alkanediol (such as monoethylene glycol). Such process is well-known and an example thereof is disclosed in U.S. Pat. No. 5,359,118. This document discloses a process in which di($C_1$-$C_4$ alkyl) carbonates and alkanediols are prepared by transesterification of an alkylene carbonate with a $C_1$-$C_4$ alkanol.

An example of an alkanol impurity that may be contained in an organic carbonate stream is an ether alkanol, for example an alkoxy alkanol. JP2003300917 and JP2002371037 relate to processes wherein dimethyl carbonate and monoethylene glycol are made from ethylene carbonate and methanol and wherein 2-methoxyethanol is formed as a by-product. In the inventions of JP2003300917 and JP2002371037, said 2-methoxyethanol is removed by specific distillation techniques.

At various points within said total process producing dialkyl carbonate from alkylene oxide via alkylene carbonate, organic carbonate streams containing one or more alkanol impurities may be produced. An example of such alkanol impurity is an ether alkanol, for example an alkoxy alkanol. For example, in a reactor where ethanol and ethylene carbonate are reacted into diethyl carbonate and monoethylene glycol, a side-reaction of ethanol with ethylene oxide, formed by back-reaction of ethylene carbonate into ethylene oxide and carbon dioxide, into 2-ethoxyethanol (ethyl oxitol) may take place. Further, ethyl oxitol may be formed by a side-reaction of ethanol with ethylene carbonate in such a way that carbon dioxide is released and ethyl oxitol is produced. Still further, a side-reaction between ethanol and monoethylene glycol may take place producing ethyl oxitol and water. Still even further, ethyl oxitol may be formed via decarboxylation of hydroxyethyl ethyl carbonate.

Therefore, the product stream from a reactor where ethanol and ethylene carbonate are reacted into diethyl carbonate and monoethylene glycol, may comprise unconverted ethanol, unconverted ethylene carbonate, diethyl carbonate, monoethylene glycol and the above-mentioned ethyl oxitol impurity.

The presence of said alkoxy alkanol impurity may be detrimental in any subsequent production process. Said alkoxy alkanol impurity may for example end up in the dialkyl carbonate that is used as a starting material for the synthesis of diphenyl carbonate from said dialkyl carbonate and phenol. For example, in a case where the dialkyl carbonate is diethyl carbonate and the alkoxy alkanol impurity is ethyl oxitol, said ethyl oxitol may react with the phenol starting material and/or with the diphenyl carbonate product.

Direct reaction of phenol and ethyl oxitol may result in the production of phenyl 2-ethoxyethyl ether, and hence in the loss of valuable phenol reactant. Further, such reaction results in the introduction of undesired chemicals in the process and therefore to separation issues.

Reaction of diphenyl carbonate with ethyl oxitol results in product loss as phenyl 2-ethoxyethyl carbonate is produced. Further, the latter product acts as a "poison" in any subsequent polymerisation of diphenyl carbonate into polycarbonate material. For example, when diphenyl carbonate is reacted with bis-phenol A (BPA), polycarbonate and phenol are formed. Diphenyl carbonate can react with BPA since phenol is a relatively good leaving group. Dialkyl carbonates (such as diethyl carbonate) however cannot be used to produce polycarbonate by reaction with BPA, since alkanols are not good leaving groups. Alkoxy alkanols (such as ethyl oxitol) are neither good leaving groups. Therefore, in case phenyl 2-ethoxyethyl carbonate is present in a diphenyl carbonate feed to be reacted with BPA, phenol will be released easily from said phenyl 2-ethoxyethyl carbonate but not ethyl oxitol which will consequently stop the polymerization process at one end of the chain. Consequently, phenyl 2-ethoxyethyl carbonate has to be removed from diphenyl carbonate before the latter is contacted with BPA.

The above exemplifies that in a case where an organic carbonate stream containing an alkanol impurity is formed, it is desired to remove said alkanol impurity before any subsequent process takes place wherein the organic carbonate is transformed into a valuable end product. For example, it is needed to remove any ethyl oxitol impurity from a diethyl carbonate stream containing said impurity before reaction of the diethyl carbonate with phenol takes place.

Referring to the above example where ethanol and ethylene carbonate have been reacted into diethyl carbonate and monoethylene glycol, the product stream also containing unconverted ethanol and ethylene carbonate and ethyl oxitol side-product, may be separated by means of distillation. The boiling points for the various components in said product stream are mentioned in the table below.

| Component | Boiling point (° C.) |
| --- | --- |
| ethanol | 78.4 |
| diethyl carbonate | 126-128 |
| ethyl oxitol | 135 |
| monoethylene glycol | 197.3 |
| ethylene carbonate | 260.4 |

The distillation as referred to above may result in a top stream containing diethyl carbonate and unconverted ethanol and a bottom stream containing monoethylene glycol and unconverted ethylene carbonate. Most likely, all of the ethyl oxitol ends up in the top stream. However, depending on the specific conditions under which distillation is carried out, part of the ethyl oxitol may end up in the bottom stream. Subsequently, said top stream may be further separated by means of distillation into a top stream containing unconverted ethanol which can be recycled to the reactor where diethyl carbonate and monoethylene glycol are produced, and a bottom stream containing diethyl carbonate and the ethyl oxitol impurity.

As discussed above, before an organic carbonate is transformed into a valuable end product in any subsequent process, the alkanol impurity has to be removed therefrom as that might interfere with said subsequent process and/or any further processes. For the above example, this means that the ethyl oxitol impurity should be removed from the bottom stream containing diethyl carbonate and the ethyl oxitol impurity. In principle, ethyl oxitol and diethyl carbonate could be separated by means of a further distillation step. However because of the small difference in boiling point between diethyl carbonate and ethyl oxitol (see above table), such separation is very cumbersome requiring many distillation steps and stages. Therefore, there is a need to find a simple method of removing an alkanol impurity from an organic carbonate stream containing such alkanol impurity.

SUMMARY OF INVENTION

Surprisingly it was found that by contacting the organic carbonate stream with a catalyst, such alkanol impurity is removed from such stream by reaction of the alkanol impurity with the organic carbonate.

Accordingly, the present invention relates to a process for removing an alkanol impurity from a stream containing an organic carbonate and the alkanol impurity, comprising contacting the stream with a catalyst to effect reaction of the alkanol impurity with the organic carbonate.

DETAILED DESCRIPTION OF THE INVENTION

The organic carbonate in the stream from which the alkanol impurity has to be removed in accordance with the present invention, may be a di($C_1$-$C_5$)alkyl carbonate, wherein the alkyl groups (straight, branched and/or cyclic) may be the same or different, such as methyl, ethyl and propyl; or a di($C_5$-$C_7$)aryl carbonate, wherein the aryl groups may be the same or different, such as phenyl; or a ($C_1$-$C_5$)alkyl ($C_5$-$C_7$) aryl carbonate, wherein the alkyl group and the aryl group are as defined above; or a cyclic ($C_1$-$C_{10}$)alkylene carbonate, such as the carbonate of ethylene, propylene, butadiene or styrene; or a mixture of such organic carbonates. Specifically, the organic carbonate is a dialkyl carbonate, more specifically diethyl carbonate.

The alkanol impurity which has to be removed from the stream containing the organic carbonate and said impurity in accordance with the present invention, may be an ether alkanol, more specifically an alkoxy alkanol, most specifically 2-ethoxyethanol, as described above.

The amount of the alkanol impurity in the stream containing the organic carbonate and said impurity may be comprised in the range of from 0.1 to 10 wt. %, specifically 0.3 to 8 wt. %, more specifically 0.5 to 6 wt. % and most specifically 0.5 to 5 wt. %.

The reaction of the alkanol impurity with the organic carbonate in the presence of a catalyst in accordance with the present invention, results in transesterification of the organic carbonate. Therefore, the catalyst that needs to be used in the process of the present invention should be a transesterification catalyst. Before the present invention is carried out, the stream containing an organic carbonate and the alkanol impurity does not contain a catalyst. More in particular, said stream does not contain a transesterification catalyst before the present invention is carried out.

The transesterification catalyst to be added in the present invention may be one of many suitable homogeneous and heterogeneous transesterification catalysts known from prior art.

For example, suitable homogeneous transesterification catalysts have been described in U.S. Pat. No. 5,359,118 and include hydrides, oxides, hydroxides, alkanolates, amides, or salts of alkali metals, i.e., lithium, sodium, potassium, rubidium and cesium. Preferred homogeneous transesterification catalysts are hydroxides or alkanolates of potassium or sodium. Other suitable homogeneous transesterification catalysts are alkali metal salts, such as acetates, propionates, butyrates, or carbonates. Suitable catalysts are described in U.S. Pat. No. 5,359,118 and the references mentioned therein, such as EP274953A, U.S. Pat. No. 3,803,201, EP1082A, and EP180387A.

As mentioned above, it is also possible to employ a heterogeneous transesterification catalyst. In the present process, the use of a heterogeneous transesterification catalyst is preferred. Suitable heterogeneous catalysts include ion exchange resins that contain functional groups. Suitable functional groups include tertiary amine groups and quaternary ammonium groups, and also sulphonic acid and carboxylic acid groups. Further suitable catalysts include alkali metal and alkaline earth metal silicates. Suitable catalysts have been disclosed in U.S. Pat. No. 4,062,884 and U.S. Pat. No. 4,691,041. The heterogeneous catalyst may be selected from ion exchange resins comprising a polystyrene matrix and tertiary amine functional groups. An example is Amberlyst A-21 (ex Rohm & Haas) comprising a polystyrene matrix to which N,N-dimethylamine groups have been attached. Eight classes of transesterification catalysts, including ion exchange resins with tertiary amine and quaternary ammonium groups, are disclosed in J F Knifton et al., J. Mol. Catal, 67 (1991) 389ff.

The heterogeneous transesterification catalyst to be used in the present invention may be a catalyst comprising an element from Group 4 (such as titanium), Group 5 (such as vanadium), Group 6 (such as chromium or molybdenum) or Group 12 (such as zinc) of the Periodic Table of the Elements, or tin or lead, or a combination of such elements, such as a combination of zinc with chromium (for example zinc chromite). Said elements may be present in the catalyst as an oxide, such as zinc oxide. Preferably, the transesterification catalyst to be used in the present invention is a heterogeneous catalyst comprising zinc.

Further transesterification conditions are known in the art and suitably include a temperature from 40 to 200° C., and a pressure from 50 to 5000 kPa (0.5 to 50 bar).

In a case where the organic carbonate is a dialkyl carbonate of formula $R_1OC(O)OR_2$ wherein $R_1$ and $R_2$ may the same or a different alkyl and the alkanol impurity is an alkanol of formula $R_3OH$ wherein $R_3$ may be an alkoxyalkyl group, the following reactions (1) and/or (2) and/or (3) may take place when practising the present invention:

$$R_1OC(O)OR_2 + R_3OH \rightarrow R_3OC(O)OR_2 + R_1OH \quad (1)$$

$$R_3OC(O)OR_2 + R_3OH \rightarrow R_3OC(O)OR_3 + R_2OH \quad (2)$$

$$2R_3OC(O)OR_2 \rightarrow R_3OC(O)OR_3 + R_2OC(O)OR_2 \quad (3)$$

In a case where said $R_1OC(O)OR_2$ is diethyl carbonate (or EtOC(O)OEt) and said $R_3OH$ is 2-ethoxyethanol (or EtOEtOH), the following reactions (1) and/or (2) and/or (3) may take place in the presence of a transesterification catalyst:

$$EtOC(O)OEt + EtOEtOH \rightarrow EtOC(O)OEtOEt + EtOH \quad (1)$$

(2)

(3)

Said EtOC(O)OEtOEt (OxEC) is a mixed carbonate, namely ethyl 2-ethoxyethyl carbonate. EtOEtOC(O)OEtOEt (DOxC) is di(2-ethoxyethyl) carbonate.

In a case where the stream containing the organic carbonate and the alkanol impurity, is a stream containing a dialkyl carbonate that has been produced from reacting an alkanol with an alkylene carbonate, the stream usually contains unconverted alkanol reactant in addition to the alkanol impurity. Reference is made to the introduction of the present specification wherein the formation of such organic carbonate stream is described.

In a case where the stream containing the organic carbonate and the alkanol impurity, is a stream containing dialkyl carbonate, unconverted alkanol and an alkanol impurity, contacting of said stream with transesterification catalyst to effect reaction of the alkanol impurity with the organic carbonate in accordance with the present invention, may be performed before, during or after the step wherein dialkyl carbonate is separated from unconverted alkanol.

Separation of the dialkyl carbonate from unconverted alkanol may be effected by means of distillation. Such distillation results in a top stream containing the unconverted alkanol (such as ethanol) and a bottom stream containing the dialkyl carbonate (such as diethyl carbonate), in a case where the unconverted alkanol has been reacted in a preceding step with an alkylene carbonate to produce the dialkyl carbonate and an alkanediol.

Preferably, said contacting with transesterification catalyst is performed during said distillation step.

In a case where said contacting with transesterification catalyst is performed during said distillation step, the catalyst for effecting reaction of the alkanol impurity with the dialkyl carbonate may be added to the distillation column itself or to a reactor of which the inlet and outlet are connected to said distillation column.

In a case where the catalyst is added to the distillation column itself, said addition preferably takes place at a position where the concentration of unconverted alkanol (such as ethanol) is relatively low (for example 0 to 0.5 wt. %) so that reaction of the dialkyl carbonate (such as diethyl carbonate) with the alkanol impurity (such as 2-ethoxyethanol) is favoured in case the latter reaction would result in the production of an alkanol (such as ethanol) which is the same as the unconverted alkanol. For example, the catalyst may be added to the reboiler section at the bottom of the distillation column.

In the case where the catalyst is added to a reactor of which the inlet and outlet are connected to said distillation column, said inlet is preferably connected to said column at a position where the concentration of unconverted alkanol in the column is relatively low, for the same reasons as described for the case where the catalyst is added to the distillation column itself.

In all of these cases, where the alkanol resulting from the reaction of the dialkyl carbonate with the alkanol impurity is the same as the unconverted alkanol, the newly formed alkanol is favourably removed overhead together with the unconverted alkanol. There is question of reactive distillation. This has the additional advantage of shifting the equilibrium of the reaction of the dialkyl carbonate with the alkanol impurity into the desired direction.

In a case where said contacting with transesterification catalyst is performed after said distillation step, the catalyst is added to the bottom stream that originates from said distillation step and which contains dialkyl carbonate but no longer unconverted alkanol. Said addition may take place in a separate reactor or in a 2nd (reactive) distillation column.

The present invention advantageously results in the removal of an alkanol impurity in organic carbonate streams, which alkanol impurity might have interfered in any subsequent process using said organic carbonate if it would not have been removed. It is recognised that by practising the present invention said alkanol impurity and (a small part of) the dialkyl carbonate is converted into another carbonate(s) and alkanol.

Where needed, said other carbonate(s) and alkanol may easily be separated from the dialkyl carbonate to be purified by methods known to the skilled person, such as distillation. Therefore, the present process may further comprise the step of removing the carbonate product resulting from the reaction of the alkanol impurity with the dialkyl carbonate, from the stream containing the dialkyl carbonate. Said carbonate product may be the product directly resulting from the reaction of the alkanol impurity with the dialkyl carbonate, or the product (s) resulting from any of the above further reactions (2) and (3). It is preferred that if said additional step is performed it is also performed in the presence of a transesterification catalyst so that above-mentioned reaction (3) may take place and/or may be completed resulting in recovery of part of the dialkyl carbonate that had reacted with the alkanol impurity before.

For example, in a case where a stream containing diethyl carbonate and 2-ethoxyethanol impurity has been contacted with a transesterification catalyst in accordance with the present invention, pure diethyl carbonate may easily be obtained by means of distillation in view of the boiling point differences between diethyl carbonate and the resultant products. This is indicated in the table below.

| Component | Boiling point (° C.) |
| --- | --- |
| ethanol | 78.4 |
| diethyl carbonate | 126-128 |
| ethyl 2-ethoxyethyl carbonate | 190.2(*) |
| di (2-ethoxyethyl) carbonate | 245.5(*) |

(*) Calculated using ACD/Labs Software V9.04 from Solaris
(©1994-2008 ACD/Labs)

Accordingly, the present invention also relates to a process for the preparation of a dialkyl carbonate and an alkanediol comprising:

(a) reacting an alkylene carbonate and an alkanol in the presence of a transesterification catalyst to obtain a product mixture containing unconverted alkylene carbonate, unconverted alkanol, dialkyl carbonate, alkanediol and an alkanol impurity;

(b) separating unconverted alkylene carbonate and alkanediol from the product mixture to obtain a top stream containing unconverted alkanol, dialkyl carbonate and the alkanol impurity;

(c) recovering the alkanediol; and (d) separating unconverted alkanol from the top stream containing unconverted alkanol, dialkyl carbonate and the alkanol impurity obtained in step (b) to obtain a bottom stream containing dialkyl carbonate and the alkanol impurity, which process further comprises (e) contacting the bottom stream containing dialkyl carbonate and the alkanol impurity obtained in step (d) with a catalyst to effect reaction of the alkanol impurity with the organic carbonate.

Accordingly, the present invention further also relates to a process for the preparation of a dialkyl carbonate and an alkanediol comprising:

(a) reacting an alkylene carbonate and an alkanol in the presence of a transesterification catalyst to obtain a product mixture containing unconverted alkylene carbonate, unconverted alkanol, dialkyl carbonate, alkanediol and an alkanol impurity;

(b) separating unconverted alkylene carbonate and alkanediol from the product mixture to obtain a top stream containing unconverted alkanol, dialkyl carbonate and the alkanol impurity;

(c) recovering the alkanediol; and (d) separating unconverted alkanol from the top stream containing unconverted alkanol, dialkyl carbonate and the alkanol impurity obtained in step (b) to obtain a bottom stream containing dialkyl carbonate, wherein during step (d), the top stream containing unconverted alkanol, dialkyl carbonate and the alkanol impurity obtained in step (b) is contacted with a catalyst to effect reaction of the alkanol impurity with the dialkyl carbonate.

All of the above-described embodiments and preferences in relation to the above-described general process for removing an alkanol impurity from a stream containing an organic carbonate and the alkanol impurity, comprising contacting the stream with a catalyst to effect reaction of the alkanol impurity with the organic carbonate, also apply to the two above-mentioned specific processes for the preparation of a dialkyl carbonate and an alkanediol, more in particular to step (e) and step (d), respectively, of said two processes.

In addition, the above-described transesterification catalyst and other transesterification conditions are equally applicable to steps (a) of said two processes for the preparation of a dialkyl carbonate and an alkanediol.

Further, the present invention relates to a process for making a diaryl carbonate, comprising contacting, in the presence of a transesterification catalyst, an aryl alcohol with a stream containing a dialkyl carbonate from which stream an alkanol impurity has been removed in accordance with any one of the above-described processes.

Still further, the present invention relates to a process for making a diaryl carbonate, comprising contacting a stream containing a dialkyl carbonate and an alkanol impurity with a catalyst to effect reaction of the alkanol impurity with the dialkyl carbonate in accordance with any one of the above-described processes, and then contacting, in the presence of a transesterification catalyst, an aryl alcohol with the stream containing the dialkyl carbonate.

Preferably, said diaryl carbonate is diphenyl carbonate and said aryl alcohol is phenol.

In addition, the above-described transesterification catalyst and other transesterification conditions are equally applicable to said process for making a diaryl carbonate.

The invention is further illustrated by the following Example.

EXAMPLE 30 g of diethyl carbonate (DEC), containing 0.8 wt. % of ethyl oxitol (EtOEtOH; 2-ethoxyethanol), and 6.08 g of a heterogeneous catalyst comprising zinc were placed in a round bottom flask under nitrogen. The resulting suspension was stirred under atmospheric pressure with a magnetic stirrer and heated at 100° C. with an oil bath, for 235 minutes. The catalyst was ZN-0312 T ⅛ (HT) catalyst supplied by BASF, which is a mixture of zinc oxide (about 65 wt. %) and zinc chromite (about 35 wt. %).

A condenser was fitted to the flask to keep any light components in the reaction mixture. At the start and at the end of the experiment, samples of the reaction mixture were taken and analyzed using GC chromatography. The analysis results are indicated in the Table below.

| Components | Amount (wt. %) at start | Amount (wt. %) at end |
|---|---|---|
| EtOC (O) OEt (DEC) | 99.2 | 98.0 |
| EtOEtOH (ethyl oxitol) | 0.8 | 0 |
| EtOC (O) OEtOEt | 0 | 1.9 |
| EtOEtOC (O) OEtOEt | 0 | trace |

From the results in the above table it appears that the 2-ethoxyethanol contaminant was quantitatively converted into ethyl 2-ethoxyethyl carbonate and a trace amount of di(2-ethoxyethyl) carbonate. The differences in boiling point between DEC and ethyl 2-ethoxyethyl carbonate and between DEC and di(2-ethoxyethyl) carbonate are such (see the 2nd table in the description preceding this Example) that said higher boiling carbonates can be easily removed from DEC, resulting in pure DEC.

What is claimed is:

1. A process for removing an alkanol impurity from a stream containing an organic carbonate and the alkanol impurity, comprising contacting the stream with a catalyst to effect reaction of the alkanol impurity with the organic carbonate, wherein the organic carbonate is a di($C_1$-$C_5$)alkyl carbonate and the alkanol impurity is an ether alkanol and wherein the stream containing an organic carbonate and the alkanol impurity is obtained by a process for the preparation of a di($C_1$-$C_5$)alkyl carbonate and an alkanediol comprising:

(a) reacting an alkylene carbonate and an alkanol in the presence of a transesterification catalyst to obtain a product mixture containing unconverted alkylene carbonate, unconverted alkanol, di($C_1$-$C_5$)alkyl carbonate, alkanediol and an alkanol impurity;

(b) separating unconverted alkylene carbonate and alkanediol from the product mixture to obtain a top stream containing unconverted alkanol, di($C_1$-$C_5$)alkyl carbonate and the alkanol impurity;

(c) recovering the alkanediol; and (d) separating unconverted alkanol from the top stream containing unconverted alkanol di($C_1$-$C_5$)alkyl carbonate and the alkanol impurity obtained in step (b) to obtain a bottom stream containing di($C_1$-$C_5$)alkyl carbonate and the alkanol impurity, which process further comprises (e) contacting the bottom stream containing di($C_1$-$C_5$)alkyl carbonate and the alkanol impurity obtained in step (d) with a catalyst to effect reaction of the alkanol impurity with the di($C_1$-$C_5$)alkyl carbonate.

2. A process according to claim 1, wherein the organic carbonate is diethyl carbonate and the alkanol impurity is 2-ethoxyethanol.

3. A process according to claim 1, wherein the catalyst is a heterogeneous catalyst.

4. A process according to claim 1, wherein the alkylene carbonate is ethylene carbonate, the unconverted alkanol is ethanol, the di($C_1$-$C_5$)alkyl carbonate is diethyl carbonate, the alkanediol is monoethylene glycol and the alkanol impurity is 2-ethoxyethanol.

5. A process according to claim 1, further comprising the step of removing the carbonate product resulting from the reaction of the alkanol impurity with the di($C_1$-$C_5$)alkyl carbonate, from the stream containing the di($C_1$-$C_5$)alkyl carbonate.

6. A process for removing an alkanol impurity from a stream containing an organic carbonate and the alkanol impurity, comprising contacting the stream with a catalyst to effect reaction of the alkanol impurity with the organic carbonate, wherein the organic carbonate is a di($C_1$-$C_5$)alkyl carbonate and the alkanol impurity is an ether alkanol and wherein the stream containing an organic carbonate and the alkanol impurity is obtained by a process for the preparation of a di($C_1$-$C_5$)alkyl carbonate and an alkanediol comprising:
  (a) reacting an alkylene carbonate and an alkanol in the presence of a transesterification catalyst to obtain a product mixture containing unconverted alkylene carbonate, unconverted alkanol, di($C_1$-$C_5$)alkyl carbonate, alkanediol and an alkanol impurity;
  (b) separating unconverted alkylene carbonate and alkanediol from the product mixture to obtain a top stream containing unconverted alkanol, di($C_1$-$C_5$)alkyl carbonate and the alkanol impurity;
  (c) recovering the alkanediol; and
  (d) separating unconverted alkanol from the top stream containing unconverted alkanol di($C_1$-$C_5$)alkyl carbonate and the alkanol impurity obtained in step (b) to obtain a bottom stream containing di($C_1$-$C_5$)alkyl carbonate, wherein during step (d), the top stream containing unconverted alkanol, di($C_1$-$C_5$)alkyl carbonate and the alkanol impurity obtained in step (b) is contacted with a catalyst to effect reaction of the alkanol impurity with di($C_1$-$C_5$)alkyl carbonate.

7. A process according to claim 6, wherein the organic carbonate is diethyl carbonate and the alkanol impurity is 2-ethoxyethanol.

8. A process according to claim 6, wherein the catalyst is a heterogeneous catalyst.

9. A process according to claim 6, wherein the alkylene carbonate is ethylene carbonate, the unconverted alkanol is ethanol, the di($C_1$-$C_5$)alkyl carbonate is diethyl carbonate, the alkanediol is monoethylene glycol and the alkanol impurity is 2-ethoxyethanol.

10. A process according to claim 6, further comprising the step of removing the carbonate product resulting from the reaction of the alkanol impurity with the di($C_1$-$C_5$)alkyl carbonate, from the stream containing the di($C_1$-$C_5$)alkyl carbonate.

* * * * *